United States Patent
Chateau et al.

(10) Patent No.: US 9,166,276 B2
(45) Date of Patent: Oct. 20, 2015

(54) MULTIFUNCTION SINGLE ANTENNA FOR CONTACTLESS SYSTEMS

(71) Applicant: Texas Instruments Incorporated, Dallas, TX (US)

(72) Inventors: Alain Bruno Chateau, Cagnes sur Mer (FR); D Georges Poissonnier, Paris (FR); Vasile Zoicas, La Gaude (FR)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 538 days.

(21) Appl. No.: 13/665,911

(22) Filed: Oct. 31, 2012

(65) Prior Publication Data

US 2014/0117927 A1 May 1, 2014

(30) Foreign Application Priority Data

Oct. 30, 2012 (EP) .................................. 12290376

(51) Int. Cl.
| | |
|---|---|
| *H02J 7/00* | (2006.01) |
| *H01Q 1/22* | (2006.01) |
| *H01Q 1/24* | (2006.01) |
| *H01Q 1/27* | (2006.01) |
| *H01Q 7/00* | (2006.01) |
| *A61B 5/0428* | (2006.01) |
| *H02J 7/02* | (2006.01) |
| *H02J 7/04* | (2006.01) |
| *H02J 17/00* | (2006.01) |
| *H01Q 5/321* | (2015.01) |
| *H04B 5/00* | (2006.01) |

(52) U.S. Cl.
CPC ............ *H01Q 1/2225* (2013.01); *A61B 5/0428* (2013.01); *H01Q 1/248* (2013.01); *H01Q 1/273* (2013.01); *H01Q 5/321* (2015.01); *H01Q 7/00* (2013.01); *H02J 7/025* (2013.01); *H02J 7/045* (2013.01); *H02J 17/00* (2013.01); *H04B 5/0075* (2013.01); *A61B 2560/0214* (2013.01); *H04B 5/0037* (2013.01)

(58) Field of Classification Search
USPC .......................................... 320/108
See application file for complete search history.

(56) References Cited

U.S. PATENT DOCUMENTS

| | | | | |
|---|---|---|---|---|
| 5,659,240 | A | * 8/1997 | King ............................ | 320/134 |
| 6,564,046 | B1 | * 5/2003 | Chateau ..................... | 455/343.1 |
| 6,947,721 | B2 | * 9/2005 | Pritchett et al. ............. | 455/343.1 |
| 2003/0038612 | A1 | * 2/2003 | Kutkut .......................... | 320/140 |
| 2003/0141845 | A1 | * 7/2003 | Krieger et al. ................ | 320/132 |
| 2008/0210762 | A1 | 9/2008 | Osada | |
| 2009/0121713 | A1 | 5/2009 | Helvoort | |

OTHER PUBLICATIONS

"Integrated Wireless Power Supply Receiver, Qi (Wireless Power Consortium) Compliant", Texas Instruments Incorporated, bq51013, SLVSAT9, Apr. 2011, pp. 1-27.

* cited by examiner

*Primary Examiner* — Yalkew Fantu
(74) *Attorney, Agent, or Firm* — Ronald O. Neerings; Frank D. Cimino

(57) ABSTRACT

A multifunction antenna is described in which the multifunction antenna is divided into a first segment and a second segment by an impedance circuit that produces low impedance at a low frequency and high impedance at a high frequency. A high frequency radio frequency (HF-RF) signal may be transmitted or received using only the first segment of the multifunction antenna from a HF-RF transceiver by blocking the HF-RF signal from the second segment by the impedance circuit. A low frequency radio frequency (LF-RF) signal may be received using both the first segment and the second segment of the multifunction antenna by passing the LF-RF signal through the impedance circuit.

20 Claims, 7 Drawing Sheets

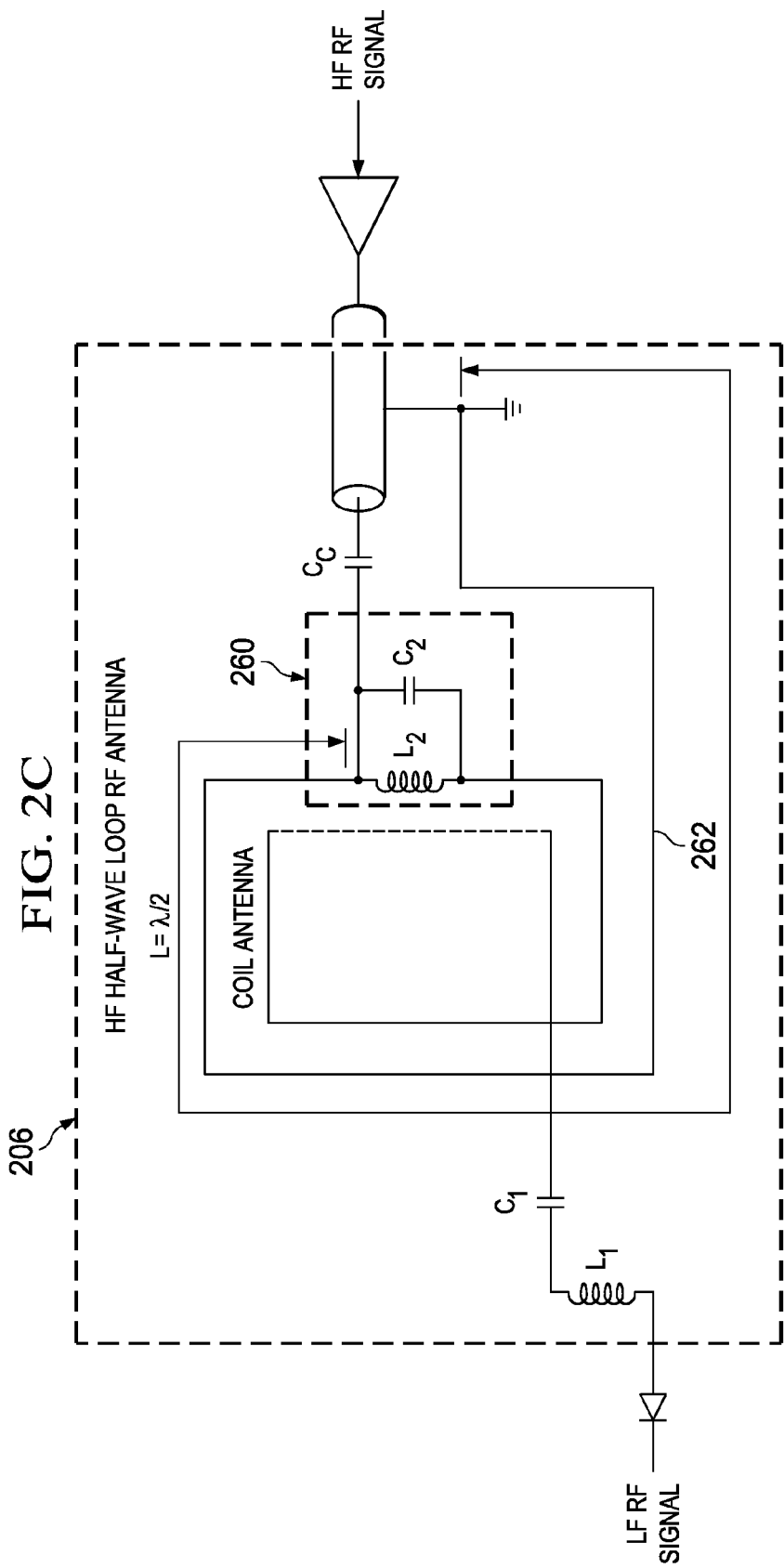

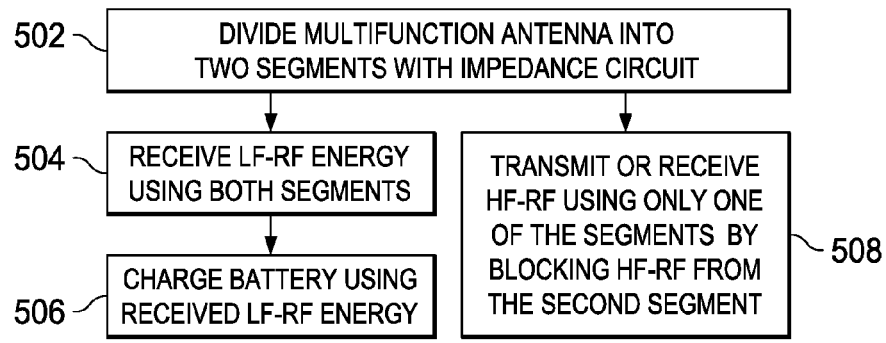
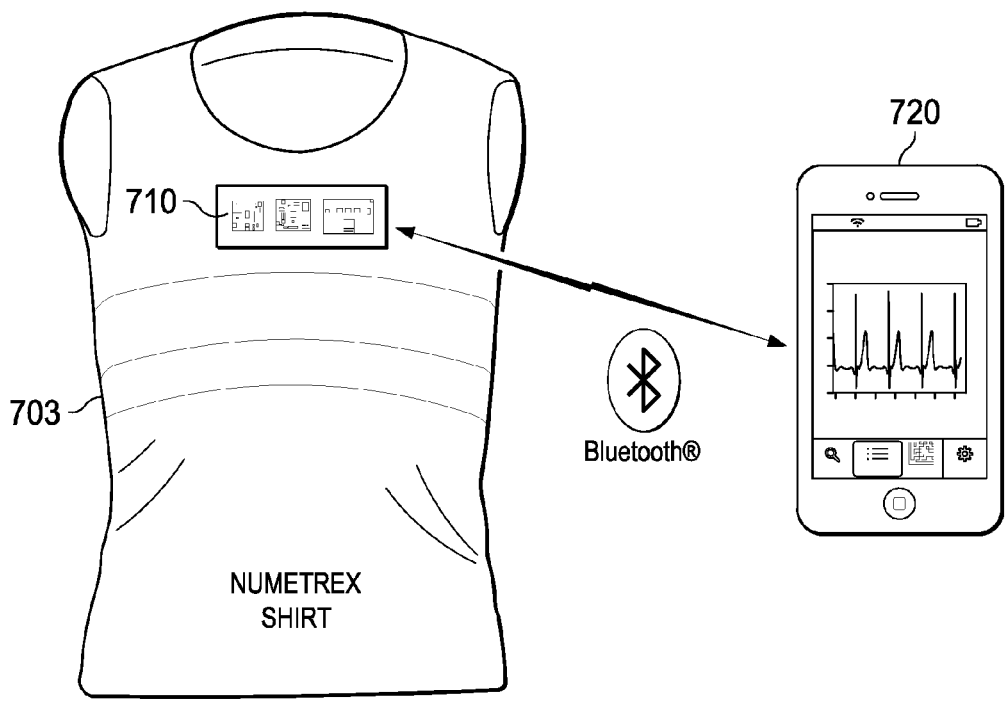

MULTIFUNCTION SINGLE ANTENNA FOR CONTACTLESS SYSTEMS

CLAIM OF PRIORITY UNDER 35 U.S.C. 119 (A)

The present application claims priority to and incorporates by reference EP Application number EP12290376.8, filed Oct. 30, 2012, entitled "Multifunction Single Antenna for Contactless Systems."

FIELD OF THE INVENTION

This invention generally relates to use of a single multi-function antenna to support both low frequency magnetic coupling and high frequency radio frequency transmission.

BACKGROUND OF THE INVENTION

Wireless energy transfer for contactless battery charging of an active mobile device and over-the-air high speed data transmission between an active mobile device and a remote access point or base station typically use two distinct radio frequency wireless transmission techniques: magnetic conductive coupling and radio-electric propagation coupling. Each of these wireless transmission techniques use a dedicated antenna design for operation within a specific radio frequency range. Magnetic conductive coupling typically operates at LF (low frequency) radio frequencies less than 10 MHz with a transmission range less than 10 cm. Radio-electric coupling typically operates at UHF radio frequencies in the range of 300 MHz up to 3-5 GHz with a transmission range greater than 1 m.

Near Field Communication (NFC) is a wireless technology allowing two devices to communicate over a short distance of approximately 10 cm or less. NFC is standardized internationally within NFC Forum specifications and defined in ISO/IEC 18092, ECMA-340, and ISO 14443, for example. NFC allows a mobile device to interact with a subscriber's immediate environment. With close-range contactless technology, mobile devices may be used as credit cards, to access public transportation, to access secured locations, and many more applications. While NFC may used for short distance communication and collecting energy to power the mobile device, the mobile device may also include a UHF-RF transceiver for longer distance communication using a separate antenna.

Contactless systems are commonly used as access control ID's (e.g. employee badges), as well as payment systems for public transportation etc. More recently, credit cards are beginning to include NFC capability. Lately, contactless capabilities are being integrated into mobile phones as well; recent examples are Nokia's 6212 phone and Google's Android, which supported NFC in its latest release.

BRIEF DESCRIPTION OF THE DRAWINGS

Particular embodiments in accordance with the invention will now be described, by way of example only, and with reference to the accompanying drawings:

FIG. 2A-2C are schematics illustrating use of a single multifunction antenna for both low frequency and high frequency operation;

FIG. 5 is a flow chart illustrating operation of a multifunction antenna; and

FIGS. 6 and 7 illustrate an example mobile device that uses a multifunction antenna.

Figure 1:
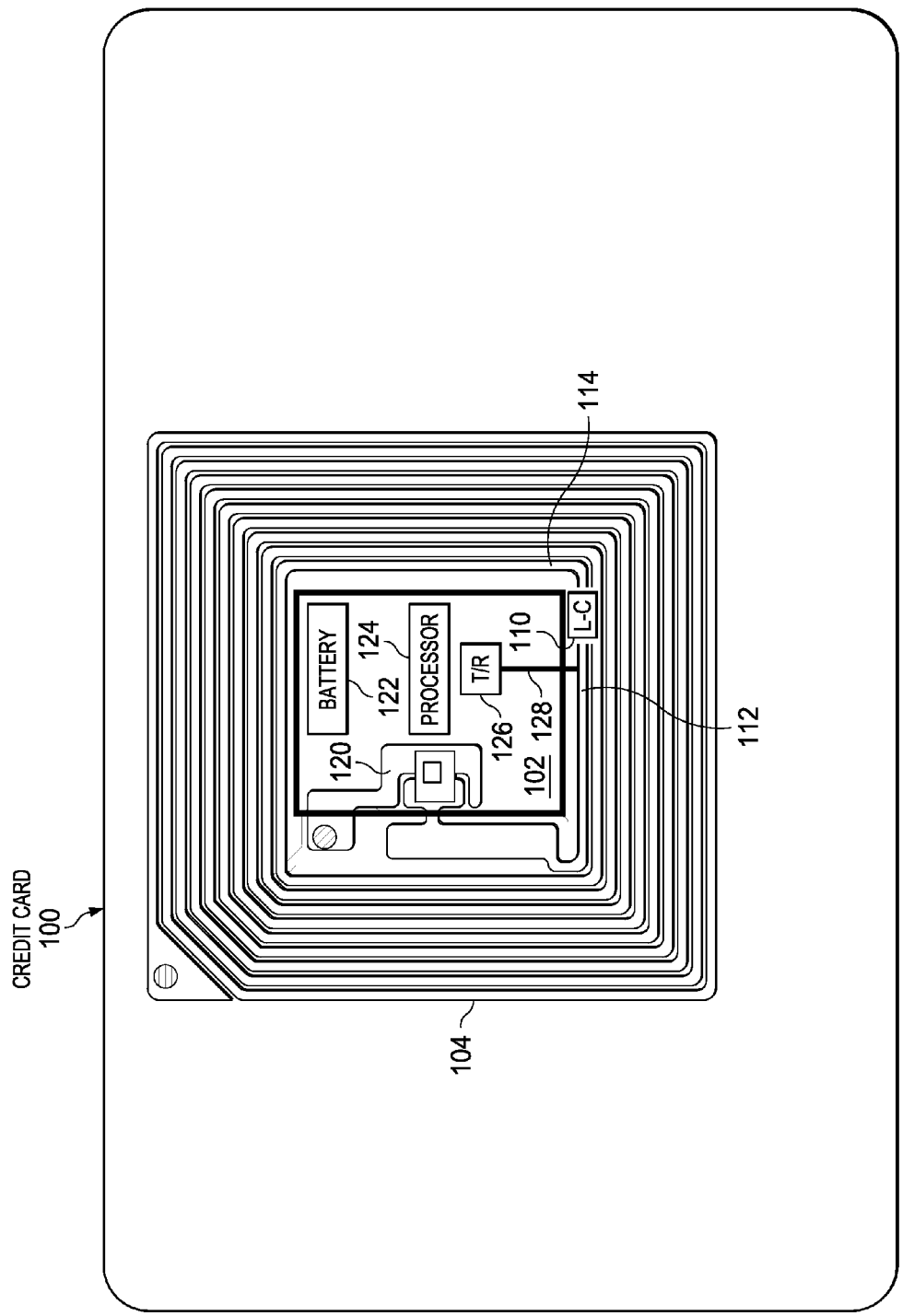
FIG. 1 is an illustration of a contactless device that uses a multifunction antenna.

Other features of the present embodiments will be apparent from the accompanying drawings and from the detailed description that follows.

DETAILED DESCRIPTION OF EMBODIMENTS OF THE INVENTION

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

The term "contactless system" in this document is intended to cover any contactless system, such as, but not limited to, NFC (near field communication), ISO14443, ISO 15693 (proximity cards), any "RFID" (radio frequency identification) system etc., that may use a lower frequency for magnetic coupling of energy for charging a battery and a higher frequency for over the air data transmission, for example.

Many new services are now being deployed that are supported by machine-to-machine communication (M2M) thanks to the high integration of wireless communication, sensing, and data processing in compact electronic devices. Beyond the now common passive RFID devices (e.g. tags), there is a need for more powerful wireless devices that have a capability to acquire, actuate, process and wirelessly transfer data in full autonomy and at high rates. For example, various embodiments may be useful in home automation, health care, security, multimedia, energy management, etc.

Over the air high data throughput typically depends upon radio frequency transmission based on electromagnetic propagation coupling in the UHF (ultra high frequency) band. Device long range autonomy requires embedded energy storage with charging capability. The use of a wireless power transfer technique based on induction technology allows further miniaturization of electronic devices by avoiding any wiring and plugs for connecting to a power charger.

Antenna configuration solutions for existing active mobile devices are based on either two antennas designed respectively for inductive coupling and propagation coupling or one antenna designed solely for inductive coupling with power transmission relying on the energy of the carrier signal and data transmission on the modulation of this carrier. The latter solution is typically used for NFC (near-field communication) application with limited transmission range <10 cm and reduced data transmission rate <500 Kbit/s.

Embodiments of the invention, as described herein, answer the challenge of the integration of a multi-function antenna system in a reduced form-factor wireless electronic device by the design of a single antenna structure supporting various wireless transmission techniques, namely: propagation coupling for data transmission, and inductive coupling for energy transmission. The layout of a single structure for a multi-functional antenna allows the adoption of advanced assembly or micro-packaging technologies such as thin flexible substrate, chip-on-board, electronic on textile printing, lamination, etc.

Various embodiments of a single antenna layout may support both RF data transmission and wireless inductive energy transfer operating in different radio frequency bands. Radio-electric coupling typically operates at high frequency (HF) radio frequencies from 300 MHz up to 3-5 GHz with a transmission range greater that one meter. Magnetic coupling typically operates at LF (low frequency) radio frequencies less than approximately 10 MHz with a transmission range less than approximately 10 cm. However, an embodiment that conforms to NFC may operate at 13.56 MHz and there are a number of catalog components available that provide inductive power charging at this frequency.

FIG. 1 is an illustration of a contactless device 100 that includes multifunction antenna 104, which in this example is representative of a credit card. A small integrated circuit 102 includes a charging circuit 120 that is coupled to coil antenna 104. In some proximity card and vicinity card embodiments, charging circuit 120 may be a simple capacitor that is charged by resonant inductive coupling via an LC circuit including capacitor 120 and coil 104 that are connected in parallel. When the card is placed in proximity to a card reader, the card reader produces an electromagnetic field that excites the coil and resonant current charges the capacitor, which in turn energizes and powers IC 102. IC 102 may also include a simple processor 124 with application software stored in read only memory. IC 102 may also include a small amount of non-volatile RAM that is used to store parameters while the card is processing a transaction.

NFC is a set of short-range wireless technologies, typically requiring a distance of 4 cm or less, that use inductive coupling of relatively low frequency (LF) radio signals to transmit charging energy and also to provide wireless data transfer. Some NFC embodiments operate at 13.56 MHz on ISO/IEC 18000-3 air interface and at rates ranging from 106 kbit/s to 424 kbit/s, for example. Other embodiments may be based on existing radio-frequency identification (RFID) contactless standards including ISO/IEC 14443 and FeliCa, for example. Embodiments may also utilize later developed standards for contactless communication. NFC involves an initiator and a target; the initiator actively generates an RF field that can power a passive target. This enables NFC targets to take very simple form factors such as tags, stickers, key fobs, or cards that do not require batteries. NFC peer-to-peer communication is possible, provided both devices are powered. NFC tags contain data and are typically read-only but may be rewriteable. They can be custom-encoded by their manufacturers or use the specifications provided by the NFC Forum, an industry association charged with promoting the technology and setting key standards. The tags can securely store personal data such as debit and credit card information, loyalty program data, PINs and networking contacts, among other information. The NFC Forum defines four types of tags which provide different communication speeds and capabilities in terms of configurability, memory, security, data retention and write endurance. Tags currently offer between 96 and 4,096 bytes of memory.

IC 102 may also include transceiver 126 that allows the card to perform longer distance data transmission via the UHF radio transmission using a portion of coil 104 as a dipole antenna. As will be described in more detail below, impedance circuit 110 is inserted in series in coil 104 to form a short segment 112 and a longer segment 114. Transceiver 126 is coupled to short segment 112 close to impedance circuit 110, as indicated at 128. Short segment 112 may be used as a dipole antenna, while the entire coil, including segment 112 and longer segment 114 may be used for inductive coupling.

In some embodiments, charging circuit 120 is coupled to a battery 122 and is operable to charge battery 122 while the card is inductively coupled to a source of energy. Battery 122 allows autonomous operation of card 100 while it is not inductively coupled to a source of energy.

Figure 2A:
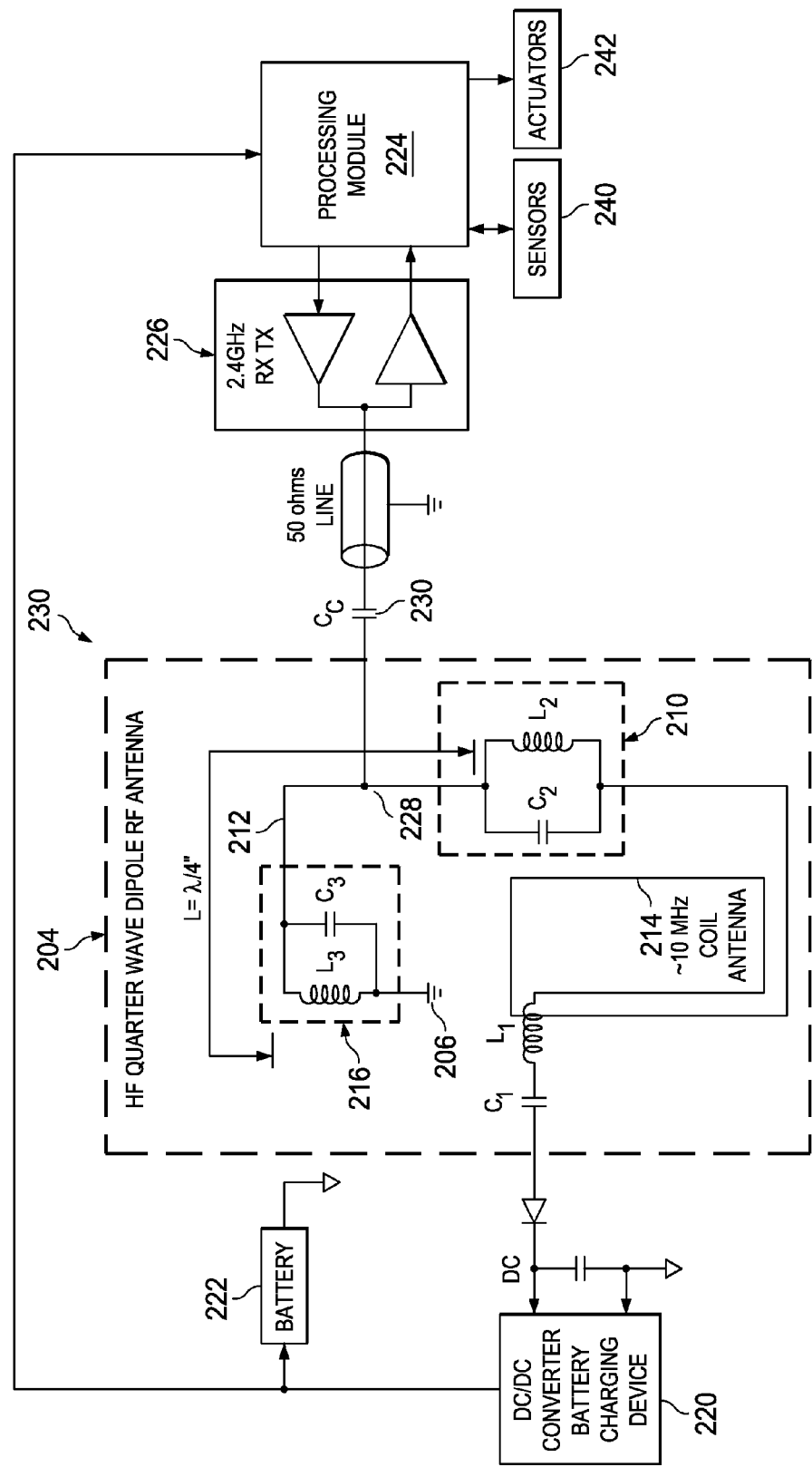

FIG. 2A is a schematic illustrating use of a single multifunction antenna 204 for both low frequency and high frequency operation. In this embodiment, transceiver 226 may transmit and receive data using a high frequency (HF) radio frequency signal. As mentioned earlier, the frequency is selected from the HF band between approximately 300 MHz and 3-5 GHz. Charging circuit 220 receives inductively coupled energy from coil 204 and thereby charges battery 222. Battery 222 may be implemented using a known or later discover energy storage technology. For example, battery 222 may be a chemical storage device, such a lithium ion battery, for example, or it may be a field storage device, such as a capacitor, for example. Energy stored in battery 222 may be used to power processing module 224 to allow processing module to execute an application that sends or receives data via transceiver 226.

Processing module 224 may include nonvolatile memory that stores an application program that is executed by a central processing unit (CPU) within processing module 224. Additional volatile or nonvolatile memory may be included within processing module 224 for storing data that is received via transceiver 226 and/or data that is received from sensors 240 that may be included within processor module 224 or coupled to processor module 224. These sensors may include, but not be limited to, sensors to measure heat, light, pressure, flow rates, electrical or magnetic field strength, pressure, etc. Actuators 242 may receive data or commands received via transceiver 226 from RF antenna segment 212. Actuator 242 may be a motion device, an illumination device, or other mechanical/electrical device. Actuator 242 may be an electrode, for example, for use in an EKG system of FIG. 6.

The multi-function antenna structure disclosed herein is based on a coil resonant antenna design suited for inductive power coupling with a portion 212 of coil 204 used as a standard dipole or similar antenna configuration suited for propagation coupling. This saves PCB (printed circuit board) area and requires only a simple impedance circuit 210 to divide coil 204 into two segments 212, 214 to thereby form dipole segment 212. In this embodiment, impedance circuit 120 comprises inductor L2 and capacitor C2 that form a parallel resonant circuit at approximately the HF frequency used by transceiver 226. Coupling capacitor $C_c$ 230 may be included to provide impedance matching for the transmission line between dipole segment 212 and transceiver 226. Coupling capacitor $C_c$ provides a low impedance to HF signals and a high impedance to LF signals.

As mentioned above, a particular embodiment may be designed to operate using a frequency selected from the UHF band between approximately 300 MHz and 3 GHz. For example, a device may be designed for Bluetooth RF communication at 2.4 GHz. At f=2.4 GHz (Bluetooth), the resonating frequency for parallel connected L2/C2 is indicated by equation (1) and an impedance produced by parallel connected L2/C2 is indicated by equation (2).

$$f_r = \frac{1}{2\cdot\pi\cdot\sqrt{L_2 C_2}} \quad (1)$$

-continued $$Z = \frac{Z_L Z_C}{Z_L + Z_C} = \frac{-j\varpi L_2}{\varpi^2 L_2 C_2} \quad (2)$$

The parameter ω, the radian frequency, is defined as: $\omega = (LC)^{-1/2}$.

For 2.4 GHz, example values may be: C2=4 pF, L2=1.1 nH. The L2-C2 circuit acts as an open circuit at a resonance frequency of 2.4 GHz since Z is infinite at the resonance frequency for a parallel L-C. A typical physical size for L2, C2 is approximately 1.0×0.5 mm or 0.6×0.3 mm, for example.

Figure 2B:
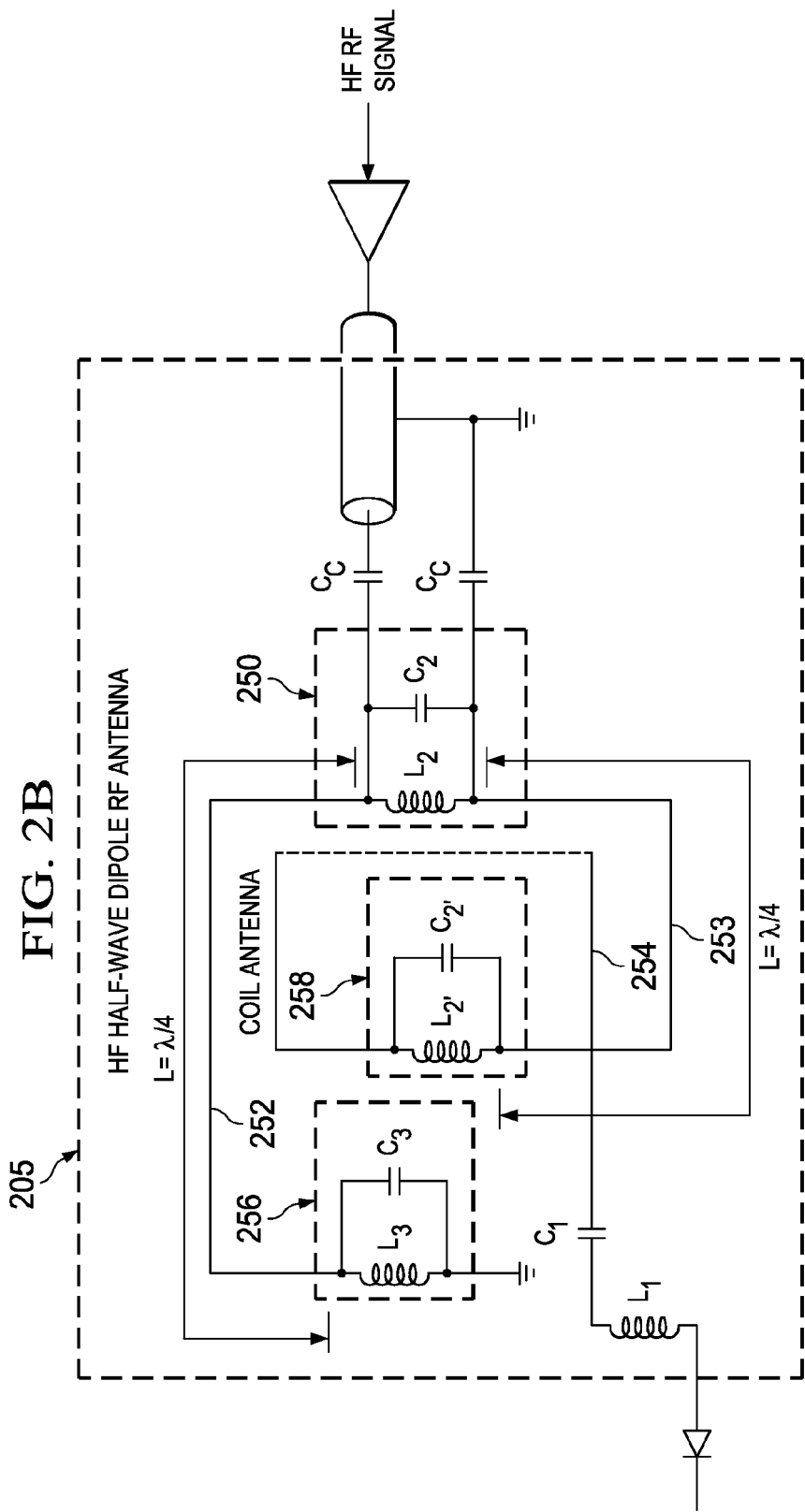

For magnetic coupling, one end of coil 204 is grounded 206 to a reference ground plane. To share a common part with coil antenna 204, the HF-RF antenna can be implemented in several different ways. Referring again to FIG. 2A, antenna 204 is configured to have a quarter wavelength dipole type HF RF antenna segment 212. In this example, tank circuits L2C2 210 and L3C3 216 exhibit high impedance (parallel resonance) at the HF RF and at RF LF frequency impedance circuits L2C2 210 and L3C3 216 are essentially shorts. Coupling capacitor $C_c$ provides a low impedance for the RF HF signal at the antenna feeding point, while blocking the LF RF from transceiver 226. The quarter wave length of segment 212 at 2.4 GHz is approximately 3.12 cm FIG. 2B illustrates a half wavelength dipole type configuration antenna 205 that may be used in place of quarter wave antenna 204. In this embodiment, impedance circuit L2'C2' 258 divides antenna 205 into two segments. The HF RF antenna segment includes two portions 252, 253 that each have a length of quarter wavelength. This configuration provides an HF RF antenna segment with a total antenna length of a half wavelength. The two ¼ length portions 252, 253 are symmetrical (mirror) around tank circuit L2C2 250. In this example, at RF HF frequency, tank circuits L2C2 250 and L3C3 256 exhibit high impedance and at LF RF frequency impedance circuits L2C2 250 and L3C3 256 are essentially shorts. Tank circuit L2'C2' 258 also exhibits high impedance at HF-RF frequency and low impedance at LF RF frequency.

FIG. 2C illustrates an antenna 206 with a half-wavelength loop type configuration segment 262 that may be used in place of quarter wave antenna 204. In this example, tank circuit L3C3 circuit is removed and the end of the antenna is directly connected to the ground reference plane. Tank circuit L2C2 260 exhibits high impedance at HF RF and at LF RF frequency impedance circuit L2C2 260 is essentially a short.

Another embodiment of a mobile device may be designed to operate in the very popular ISM (industrial, scientific, medical) band at 433 MHz (region1: Europe/Russia/Middle East/Africa), for example. At 433 MHz, dipole antenna 212 will be 17 cm long for quarter-wave, while antenna segments 252, 253 together will be 35 cm long for the half-wave dipole configuration. Similarly, halfwave loop segment 262 will be 35 cm long for half-wave. With these lengths, it becomes very efficient to combine both the dipole and the coil antennas in one footprint.

For magnetic coupling to transfer energy to charging circuit 220, and because LF charging energy is only being transmitted a very short distance, inductor L1 and capacitor C1 are calculated to offer the best quality factor for coil antenna 204 to produce magnetic coupling. For example, for charging at 10 MHz, L1 and C1 are selected to be a serial resonant circuit and therefore act as a short at 10 MHz.

For example, values of L1=6 nH and C=40 nF will produce a resonating frequency of 10.3 MHz. At this low frequency, serial inductors L2 and L3 will offer low impedance.

In an example embodiment designed for magnetic coupling in 10 MHz frequency operating range, coil antenna 204, a part of it being common with the RF dipole antenna segment 212, may be implemented using between three and ten turns.

For data transmission based on magnetic coupling as used in NFC, the antenna quality factor must be sub-optimal to obtain the necessary bandwidth for data transmission at the penalty of poor power transfer efficiency. It would be difficult to demodulate a low frequency data signal with a high Q factor corresponding to high power transfer efficiency. For example, three-five turns may be preferred for optimal energy transfer, whereas a lower number of turns, such as one, may be preferred for pure data transmission.

The frequency range of the charging energy magnetically coupled into the coil antenna will typically be in the range of 100 KHz to 10 MHz with the maximum power transferred being independent of the operating frequency in that frequency range. The selection of the optimal resonance frequency is very implementation related. An example of charging circuit 220 is available from Texas Instruments, Inc; BQ512013 is a power receiver device that is typically operated in the range of [100-300] KHz.

Table 1 summarizes the function of each of the components of associated with multifunction antenna 204 for the 2.4 GHz example. Because of the different frequency ranges used for dual-mode operation of the antenna, both wireless data transfer and wireless power charging functions can be supported concurrently.

TABLE 1

| Multifunction antenna 204 components | |
|---|---|
| HF-RF dipole @2.4 GHz (radio communication) | LF-RF magnetic coupling coil @10 MHz (wireless energy transfer) |
| $L_3$ -> dipole antenna quality factor adjustment (optional) | $L_1$ -> receiver coil quality factor |
| $L_2C_2$ resonance (Z>>) = open | $C_1$ -> receiver coil resonance |
| $L'_2C'_2$ resonance (Z>>) = open | $L_1, L_2, L_2', L_3$ = short |
| $C_C$ (Z<<) = short | $C_C$ (Z>>) = open |
| Range is greater than one meter | Range is short, typically less than 10 cm |

A typical device using this frequency may be a wireless smart card, a watch, a chest badge. etc., in other words a small dimension device. Even a wireless power rechargeable mouse would benefit from such a dual mode antenna design.

Figure 3:
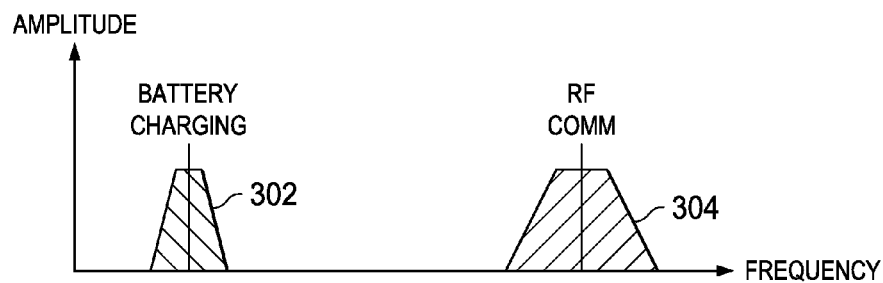
FIG. 3 is a plot illustrating example frequency bands that may be used with the antenna of FIG. 2.

FIG. 3 is a plot illustrating example frequency bands that may used with the antenna of FIG. 2. Frequency band 302 represents LF-RF signals over which energy is magnetically coupled to a coil antenna within a mobile device for use in charging a battery within the mobile device. As discussed previously, frequency band 302 is generally in the range of 100 KHz-10 MHz; however, frequency band 302 may extend higher, such as 13.56 MHZ for use with NFC compatible devices.

Frequency band 304 represents HF-RF signals over which high speed data transmission to remote targets may be performed. As discussed previously, frequency band 304 is generally in the range of 300 MHz up to 3-5 GHz with a transmission range greater that one meter.

Figure 4:
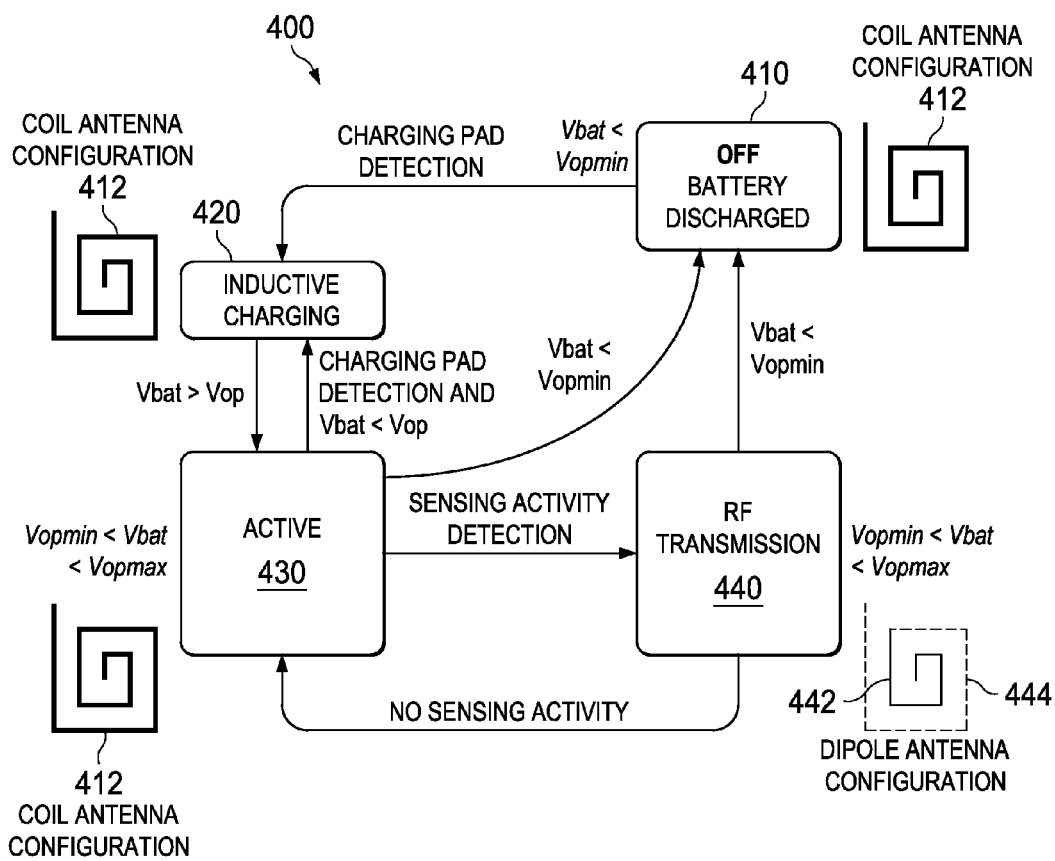
FIG. 4 is a state diagram illustrating operation of a multifunction antenna.

FIG. 4 is a state diagram 400 illustrating operation of a mobile device, such as mobile device 200, that includes a multifunction antenna as described herein. Initially, the mobile device may be in off state 410 in which the battery is discharged, or has less than a minimum operating voltage Vopmin. While the battery is discharged, the mobile device does not transmit or receive data.

When the mobile device is moved near a charging pad, coil antenna 412 will magnetically couple to LF-RF energy emanating from the charging pad. When such emanations are detected, the device will move to inductive charge state 420 and will receive charging energy from the charging pad using the entire coil antenna 412.

Once the battery is charged to a voltage Vbat that is approximate to a minimum operating voltage Vop, the device transitions to active state 430 in which charging may continue as long as the device is near the charging pad whenever the battery voltage drops below Vopmax. Battery charging control circuitry, such as charging circuit 220, in the mobile device will limit the amount of charge to maximum battery voltage of Vopmax so as not to damage the battery. Vop as the minimum battery voltage to enable operation (sensing/processing and/or RF communication). Vop is a threshold voltage to both enable device operation battery voltage is greater than battery voltage is less than Vopmin. Charging will stop when battery voltage is greater than Vopmax.

While in the active state 430, an onboard processing module, such as processing logic 224, may execute an application program that interrogates various sensors depending on the intended use/function of the mobile device.

The application program may request transmission or reception of data via a HF-RF transceiver, such as transceiver 226. At this point, the mobile device transitions to RF transmission state 440 and transmits and/or receives data using dipole antenna configuration 442, which is only a short segment of antenna coil 412. While performing HF-RF data transmissions, the HF-RF signal is blocked from the larger segment 444 by an impedance circuit, as described in more detail above. However, as described above in more detail, the mobile device may continue to receive LF-RF to recharge the battery using the entire coil antenna 412 at the same time that HF-RF signal is being transmitted/received on dipole segment 442. Additionally, an onboard processing module, such as processing logic 224, may execute (concurrently) an application program that interrogates various sensors depending on the intended use/function of the mobile device.

When there is no data to transmit/receive, the mobile device transitions back to active state 430. When the mobile device is not in the vicinity of a charging pad, the battery may discharge over time. When the battery voltage falls below minimum operating voltage Vopmin, the mobile device transitions back to off state 410.

FIG. 5 is a flow chart illustrating operation of a multifunction antenna. As described in more detail above, the multifunction antenna is divided 502 into a first segment and a second segment by an impedance circuit that produces low impedance at a low frequency and high impedance at a high frequency.

A high frequency radio frequency (HF-RF) signal may be transmitted or received 508 using only the first segment of the multifunction antenna from a HF-RF transceiver by blocking the HF-RF signal from the second segment by the impedance circuit.

A low frequency radio frequency (LF-RF) signal may be received 504 using both the first segment and the second segment of the multifunction antenna by passing the LF-RF signal through the impedance circuit. A battery may be charged 506 using the received energy. The entire multifunction antenna may be used to receive LF-RF energy via magnetic induction for charging the battery 506 while only the first segment is used to transit or receive 508 a HF-RF signal.

System Example

Figure 6:
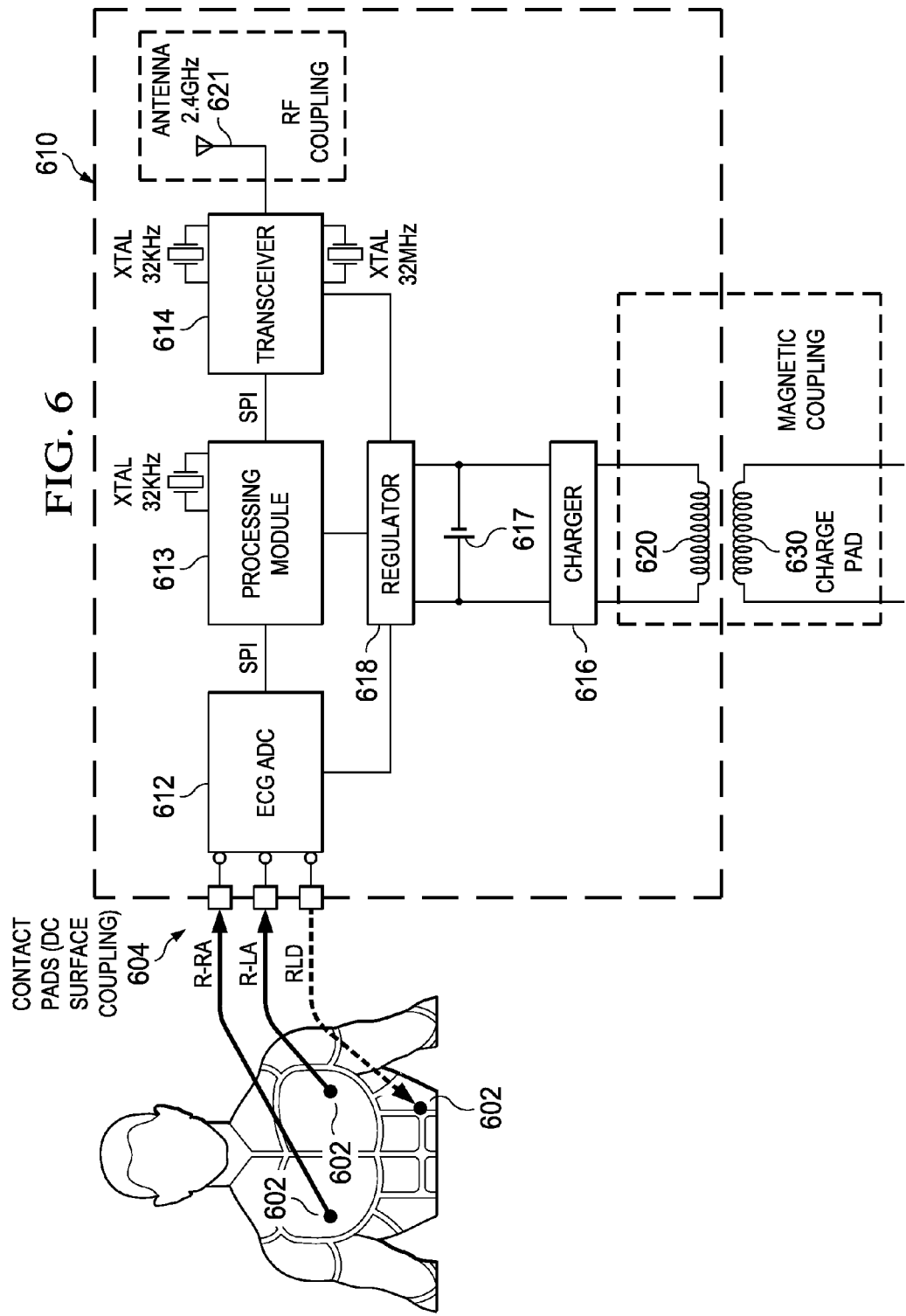

FIGS. 6 and 7 illustrate an embodiment of a mobile device 610 that may be used to sense ECG (electrocardiogram) data and transmit it to a remote monitoring system. In this example, analog front end module 612 is coupled to a set of termination points 604 that includes electrodes that are arranged to make skin contact with a subject. Analog front end module 612 may be implemented using an ADS1292 ECG ADC (analog to digital converter) available from Texas Instruments, for example. Processing module 613 may receive the ECG data and process it to determine heart rate and waveform characteristics that may be of interest to a cardiologist, for example. Processing module 613 may be implemented using a low power dissipation processor MSP430BTS5xxx available from Texas Instruments, for example. The heart rate and other waveform information may be transmitted to a remote monitoring station by transceiver 614 using 2.4 GHz dipole antenna 615. Transceiver 614 may be implemented using a Bluetooth module CC2541, available from Texas Instruments, for example.

Mobile device 610 may receive energy from a charging pad 630 using magnetic coupling, as described in more detail above. Coil antenna 620 within mobile device 610 may be magnetically coupled to another coil antenna within charge pad 630 whenever mobile device 610 is within approximately 10 cm or less to charging pad 630, for example. Charging circuit 616 converts the received energy into a voltage that is used to charge battery 617. Charging circuit 617 may be implemented using charging module BQ51013 available from Texas Instruments, for example. Regulator circuit 618 provides a regulated voltage source derived from battery 617 to modules 612-614. In this example, battery 617 is a thin-Film Li-Ion battery (h<0.4 mm). Regulator circuit 618 may be implemented using regulator module TP65xxx available from Texas Instruments, for example. In some embodiments of mobile device 610, a USB or other form of wired interconnect may be provided for an alternate source of charging energy when a charge pad is not available. Charging pad 630 may be the same or similar to those currently available for mice or smart phones As described in more detail above, dipole antenna 621 is implemented as a short segment portion of coil antenna 620 by inserting an impedance circuit in coil antenna 620 to divide it into two segments. This allows the entire coil antenna 620 to be used to receive charging energy from charge pad 630, while simultaneously use the short segment as dipole antenna 621 for transmitting/receiving HF-RF signals.

FIG. 7 illustrates another embodiment of an ECG monitoring system that uses a multifunction antenna. In this example, mobile device 710, which is similar to mobile device 610, is coupled to a set of termination points on shirt 703 that includes electrodes that are affixed to the shirt and arranged to make skin contact with a subject when shirt 703 is worn by the subject. An example of shirt 703 is a NuMetrex shirt or sports bra that is suitably modified to carry analog front end module 710.

Analog front end module 710 is configured to wirelessly transmit ECG data collected from a subject that is wearing shirt 603 to a nearby blue tooth receiver located in smart phone 720, for example. Smart phone 720 is configured with an ECG app, and may thereby process and display the ECG data in real time and also transmit the ECG data to a remote site for analysis by a cardiologist or other health care provider.

Module device 710 is connected to garment 703 with attachment pads in a way such as it can be easily removed for power charging. Signal connectivity to textile sensors embedded in the garment may be, for example, based on conductive Velcro. In another embodiment, a pocket may be provided into which mobile device 710 is placed and face-to-face coils may thereby provide capacitive coupling. Typically, the mobile device would be removed from the garment to allow washing of the garment and charging of the mobile device.

In a wearable module device, such as a smart health card, sensing and actuating signal connectivity is located on the body/garment side and the LF/HF-RF multi-mode antenna is located on the open side to optimize radio propagation in the open to the remote equipment and to reduce radio propagation to the body. In most of the cases, sensing is coupled to stimulation (actuation) such as in ECG, where an electrode RLD is used as ac output to set a reference skin voltage to reduce noise artifacts when sensing with input Left and Right electrodes.

Other Embodiments

While the invention has been described with reference to illustrative embodiments, this description is not intended to be construed in a limiting sense. Various other embodiments of the invention will be apparent to persons skilled in the art upon reference to this description. For example, other portable, or mobile systems such as remote controls, access badges and fobs, smart credit/debit cards and emulators, smart phones, digital assistants, and any other now known or later developed portable systems may embody a multifunction antenna that because of the different frequency ranges used for dual-mode operation of the antenna, both wireless data transfer and wireless power charging functions can be supported concurrently.

The techniques described in this disclosure may be implemented in hardware, software, firmware, or any combination thereof. If implemented in software, the software may be executed in one or more processors, such as a microprocessor, application specific integrated circuit (ASIC), field programmable gate array (FPGA), or digital signal processor (DSP). The software that executes the techniques may be initially stored in a computer-readable medium such as compact disc (CD), a diskette, a tape, a file, memory, or any other computer readable storage device and loaded and executed in the processor. In some cases, the software may also be sold in a computer program product, which includes the computer-readable medium and packaging materials for the computer-readable medium. In some cases, the software instructions may be distributed via removable computer readable media (e.g., floppy disk, optical disk, flash memory, USB key), via a transmission path from computer readable media on another digital system, etc.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the preceding discussion and in the claims, the terms "including" and "comprising" are used in an open-ended fashion, and thus should be interpreted to mean "including, but not limited to . . . . " Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection, for example.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A mobile device comprising:
    an energy storage device configured to receive energy from a low frequency (LF) radio frequency (RF) signal;
    a high frequency (HF) RF transceiver coupled to a processing module, wherein the energy storage device is coupled to provide power to the storage module and to the HF-RF transceiver; and
    a multifunction antenna coupled to the HF-RF transceiver and coupled to the energy storage device, wherein one end of the multifunction antenna is grounded and the energy storage device is coupled to an opposite end of the multifunction antenna, and wherein the multifunction antenna is divided into a first segment and a second segment by a first impedance circuit and the HF-RF transceiver is coupled to the multifunction antenna adjacent to the first impedance circuit.

2. The mobile device of claim 1, wherein the first impedance circuit comprises an inductor (L2) and a capacitor (C2) configured to be resonant at approximately the high frequency, such that high impedance is presented to a HF-RF signal from the transceiver and low impedance is presented to the LF-RF signal.

3. The mobile device of claim 1, wherein the first segment of the multifunction antenna between the grounded end and the first impedance circuit has a length of approximately ½ wavelength of the HF-RF signal.

4. The mobile device of claim 1, further comprising:
    a second impedance circuit connected in series with the antenna in proximity to the grounded end, wherein the impedance of the second impedance circuit is low for the LF-RF signal and wherein the impedance of the second impedance circuit is high for a HF-RF signal; and
    wherein the first segment of the multifunction antenna between the second impedance circuit and the first impedance circuit has a length of approximately ¼ wavelength of the HF-RF signal.

5. The mobile device of claim 4, further comprising:
    a third impedance circuit dividing the second segment into a third segment and a fourth segment, wherein the third impedance circuit presents a high impedance to a HF-RF signal and presents a low impedance to the LF-RF signal; and
    wherein the first segment of the multifunction antenna between the second impedance circuit and the first impedance circuit has a length of approximately ¼ wavelength of the HF-RF signal and the third segment of the multifunction antenna between the first impedance circuit and the third impedance circuit has a length of approximately ¼ wavelength of the HF-RF signal.

6. The mobile device of claim 1, wherein the low frequency is less than approximately 10 MHz.

7. The mobile device of claim 1, wherein the energy storage device comprises a battery coupled to a battery charging circuit.

8. The mobile device of claim 1, wherein the processing module comprises storage circuitry.

9. The mobile device of claim 1, further comprising a data sensing module coupled to the processing module.

10. The mobile device of claim 9, wherein the sensing module is configured to collect electrocardiogram data.

11. The mobile device of claim 1, further comprising an actuating module coupled to the processing module.

12. The mobile device of claim 11, wherein the actuating module is an electrode for an electrocardiogram device.

13. The mobile device of claim 12, further comprising a set of attachment pads coupled to the sensing module for attaching the mobile device to a garment.

14. A method for using a multifunction antenna in a mobile device, the method comprising:
    dividing the multifunction antenna into a first segment and a second segment by a first impedance circuit that produces low impedance at a low frequency and high impedance at a high frequency;
    transmitting or receiving a high frequency radio frequency (HF-RF) signal using only the first segment of the multifunction antenna from a HF-RF transceiver by blocking the HF-RF signal from the second segment by the impedance circuit; and
    receiving a low frequency radio frequency (LF-RF) signal using both the first segment and the second segment of the multifunction antenna by passing the LF-RF signal through the first impedance circuit.

15. The method of claim 14, further comprising using energy derived from the LF-RF signal to charge a battery, wherein the entire multifunction antenna is used to receive LF-RF energy via magnetic induction for charging the battery while only the first segment is used to transit or receive the HF-RF signal.

16. The method of claim 15, wherein the first segment of the multifunction antenna between the grounded end and the first impedance circuit has a length of approximately ½ wavelength of the HF-RF signal.

17. The method of claim 15, further comprising forming a dipole HF antenna configuration by using a second impedance circuit coupled in series with the first segment of the multifunction antenna to provide low impedance to a ground plane for the LF-RF signal and high impedance to the ground plane for the HF-RF signal; and
    wherein the HF-RF transceiver is coupled to the first segment proximate the first impedance network and wherein the first segment of the multifunction antenna has a length of approximately ¼ wavelength of the HF-RF signal.

18. The method of claim 17, further comprising:
    dividing the second segment into a two segments using a third impedance circuit, wherein the third impedance circuit presents a high impedance to the HF-RF signal and presents a low impedance to the LF-RF signal; and
    wherein the first segment of the multifunction antenna between the second impedance circuit and the first impedance circuit has a length of approximately ¼ wavelength of the HF-RF signal and a second segment of the multifunction antenna between the first impedance circuit and the third impedance circuit has a length of approximately ¼ wavelength of the HF-RF signal.

19. The method of claim 14, further comprising:
    receiving data from a sensor module in the mobile device;
    processing the data using a processor in the mobile device with energy from the battery; and
    providing the processed data to the HF-RF transceiver for transmission.

20. The method of claim 14, further comprising:
    receiving data from the HF-RF transceiver; and
    stimulating an actuator module in the mobile device using the received data.

\* \* \* \* \*